(12) United States Patent
Morimoto

(10) Patent No.: US 9,398,843 B2
(45) Date of Patent: Jul. 26, 2016

(54) ULTRASONIC ENDOSCOPE

(75) Inventor: Yasuhiko Morimoto, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 13/153,022

(22) Filed: Jun. 3, 2011

(65) Prior Publication Data

US 2011/0301413 A1 Dec. 8, 2011

(30) Foreign Application Priority Data

Jun. 7, 2010 (JP) ................................ P2010-129616

(51) Int. Cl.
*A61B 1/00* (2006.01)
*A61B 1/06* (2006.01)
*A61B 1/018* (2006.01)
*A61B 8/12* (2006.01)
*A61B 8/00* (2006.01)

(52) U.S. Cl.
CPC ............ *A61B 1/018* (2013.01); *A61B 1/00087* (2013.01); *A61B 8/12* (2013.01); *A61B 8/445* (2013.01)

(58) Field of Classification Search
USPC ................. 600/113, 104, 107, 109, 129, 139, 600/170–172, 437, 462–463
See application file for complete search history.

(56) References Cited

U.S. PATENT DOCUMENTS

| | | | |
|---|---|---|---|
| 5,916,148 A * | 6/1999 | Tsuyuki ........................ | 600/176 |
| 6,416,463 B1 * | 7/2002 | Tsuzuki et al. ............... | 600/130 |
| 6,547,722 B1 * | 4/2003 | Higuma et al. ............... | 600/133 |
| 6,695,775 B2 * | 2/2004 | Watanabe et al. ............. | 600/176 |
| 6,767,322 B1 * | 7/2004 | Futatsugi et al. ............. | 600/133 |
| 2005/0228289 A1 * | 10/2005 | Kohno .......................... | 600/463 |
| 2006/0009681 A1 * | 1/2006 | Tanaka et al. ................. | 600/160 |
| 2006/0025691 A1 * | 2/2006 | Tanaka et al. ................. | 600/459 |
| 2006/0183977 A1 * | 8/2006 | Ishigami et al. .............. | 600/179 |
| 2006/0241481 A1 * | 10/2006 | Itoi ............................... | 600/466 |
| 2007/0249940 A1 * | 10/2007 | Kohno .......................... | 600/463 |
| 2008/0077017 A1 * | 3/2008 | Hyuga .......................... | 600/459 |

FOREIGN PATENT DOCUMENTS

| | | |
|---|---|---|
| JP | 2003-169775 A | 6/2003 |
| JP | 2007-252458 A | 10/2007 |
| JP | 2008-253789 A | 10/2008 |

OTHER PUBLICATIONS

JP 2003-169775 "Electronic Endoscope" Kojima et al. Jun. 17, 2003 "English Machine Translation Document".*
Notice of Reasons for Rejection issued in the corresponding JP Application No. 2011-109320 on Apr. 23, 2014.

(Continued)

*Primary Examiner* — John P Leubecker
*Assistant Examiner* — Arnaldo Torres Diaz
(74) *Attorney, Agent, or Firm* — Birch, Stewart, Kolasch & Birch, LLP

(57) ABSTRACT

An observation unit can be stably held in a state where the observation unit is mounted on a distal portion, and can be easily removed without interfering with a connection pipe. A mounting hole for mounting an observation unit on a distal end body which constitutes a distal portion is formed. The mounting hole is formed with a first holding portion into which the distal portion of the lens barrel is inserted, a second holding portion into which a prism holder is inserted, and a releasing portion having a space larger than the external diameter of the lens barrel between the first and second holding portions.

23 Claims, 9 Drawing Sheets

(56) References Cited

OTHER PUBLICATIONS

Chinese Office Action issued in Chinese Application No. 201110153850.1 on Sep. 16, 2014.

Chinese Office Action issued in Chinese Application No. 201110153850.1 on Mar. 2, 2015.

Japanese Office Action issued in Japanese Application No. 2011-109320 on Dec. 24, 2014.

* cited by examiner

ULTRASONIC ENDOSCOPE

BACKGROUND OF THE INVENTION

1. Field of the Invention

The present invention relates to an endoscope in which the distal portion of the insertion part is provided with an endoscope observation mechanism.

2. Description of the Related Art

Endoscopes are configured such that the insertion part composed of a flexible portion, a bending portion, and a distal portion is provided so as to be connected to a main body operating part, and an endoscope observation mechanism is provided at the distal portion. Among these endoscopes, an endoscope is disclosed in JP2007-252458A. In this JP2007-252458A, an endoscope observation mechanism is of an oblique-front-viewing type in which the observation visual field is set to be obliquely forward.

When ultrasonic scanning is performed within the body of a subject by using an ultrasonic transducer which constitutes an ultrasonic observation mechanism, if an affected part or a part suspected to be an affected part is detected, this is used as a region of interest, living cells of this region of interest are sampled, and treatment, such as injection of a medical fluid is performed as necessary. For this reason, a puncture treatment tool is used. The puncture treatment tool is configured such that a hard pipe having a predetermined length is provided so as to be connected to the distal portion of a catheter, and the tip of this hard pipe is formed as a sharp needle point. Here, the puncture treatment tool is led out of a treatment tool outlet provided in the distal portion. However, in order to perform the lead-out under the observation by an endoscope observation mechanism and an ultrasonic observation mechanism, the puncture treatment tool has the oblique frontal lead-out direction.

In order to lead out various kinds of treatment tools including the puncture treatment tool, a treatment tool insertion channel is provided within an insertion part. In this case, a treatment tool insertion tube made of a flexible member in the bending direction is provided inside a flexible portion and a bending portion in the insertion part. The distal portion is provided at this distal end body, and a treatment tool insertion passage is bored in the distal end body. The treatment tool insertion tube and the treatment tool insertion passage are connected together by a connection pipe made of a hard member. Here, since the treatment tool insertion tube extends in the axial direction of the insertion part, and the treatment tool insertion passage is a passage which is directed to the oblique frontal direction in the distal end body, the connection pipe is made of a bending pipe, and thereby the treatment tool insertion tube which extends in the axial direction of the insertion part is changed in direction so as to face the oblique frontal direction.

An endoscope observation mechanism in an endoscope (hereinafter referred to as an ultrasonic endoscope) including an ultrasonic observation mechanism is constituted by an illumination portion and an observation portion. An emitting end of a light guide which transmits the illumination light from a light source unit faces the illumination portion. The observation portion disclosed in JP2007-252458A is configured such that a lens barrel with mounted objective lenses is mounted on a distal end body, a prism is connected to the proximal end of this lens barrel via a prism holder, and a solid state imaging element and its printed circuit board which serve as imaging sections are fixed and provided to the prism. A plurality of signal cables is connected to the printed circuit board, these signal cables are bundled, and are extended to a universal cord, which is provided so as to be connected to a main body operating part, via the main body operating part from the insertion part. In this way, the lens barrel provided with the objective lenses, the prism holder and the prism, the solid state imaging element and its printed circuit board which are imaging sections are unitized and constituted as an observation unit. The observation unit is inserted into the mounting hole bored in the distal end body, and is fixed and held by means such as adhesion. The lens barrel is inserted into this mounting hole, and the prism holder, the prism, and the imaging sections do not have special fixing portions, and are fixed to the distal end body via the lens barrel.

SUMMARY OF THE INVENTION

Meanwhile, when performing maintenance, such as repairs of the insertion part, the observation unit may be removed from the distal portion. Since the prism holder having a larger size than the external diameter of the lens barrel is provided so as to be connected to the lens barrel, and the solid state imaging element and its printed circuit board are connected together, the observation unit is not pulled out to the treatment tool outlet side.

A connection pipe which constitutes the treatment tool insertion channel is arranged on the main body operating part side (hereinafter referred to as the proximal side) of the observation unit. Thus, when the observation unit is moved to the proximal side along the mounting hole, there is a concern that the observation unit may interfere with the connection pipe made of a bending pipe. Accordingly, when the observation unit is separated from the distal end body, in order to keep the connection pipe from becoming a hindrance, it is necessary to space the connection pipe apart from the observation unit, or shorten the length by which the lens barrel is held by the mounting hole. However, when the distance between the observation unit and the connection pipe is lengthened, the distal portion in the insertion part lengthens by an equivalent amount, and when the length of the lens barrel held by the mounting hole is shortened, the stability of holding of the observation unit deteriorates. Additionally, in a direct-viewing-type endoscope which does not include the ultrasonic observation mechanism, when the observation unit interferes with the connection pipe, the observation unit may not be pulled out straight to the proximal side.

Particularly, in the case of an ultrasonic endoscope for bronchi, an insertion path becomes a thin conduit called a bronchus, demand for reducing the diameter and shortening the length of the distal portion is high. Additionally, in the thin insertion part, mounting portions of the connection pipe and the observation unit are in proximity to each other. Therefore, when the observation unit is removed, the concern that the connection pipe may become a hindrance and the observation unit may be unable to be taken out becomes greater.

The present invention has been made in view of the above points, and the object thereof is to provide an observation unit which can be stably held in a state where the observation unit is mounted on the distal portion, and can be easily removed without interfering with a connection pipe.

In order to achieve the aforementioned object, the present invention provides an endoscope having an endoscope observation mechanism at the distal portion of an insertion part, having an opening for a treatment tool outlet at the distal end body, and having a treatment tool insertion channel through which a treatment tool is led out of the treatment tool outlet. The endoscope observation mechanism comprises an observation unit including a lens barrel on which objective lenses are mounted, and imaging sections picking up the forming image of the objective lenses. The distal end body is provided with a mounting hole for mounting the observation unit. The mounting hole has a first holding portion which holds a portion of the lens barrel of the observation unit on the distal side, and a second holding portion which is formed on the side of the first holding portion separated from the distal portion, and partially holds the observation unit. Moreover, the diameter of the first holding portion is smaller than the diameter of the second holding portion, and the mounting hole and the lens barrel are separated from each other between the first and second holding portions.

A portion of a distal portion of the endoscope observation mechanism is formed with a rising portion, and mounting hole for mounting the lens barrel is formed on the rising portion. The treatment tool outlet can also be made to open to a region where the endoscope observation mechanism is mounted. In the case of an ultrasonic endoscope, a planar portion can be provided between the ultrasonic observation mechanism and the endoscope observation mechanism, and the treatment tool outlet can be made to open to this planar portion.

A distal portion of the lens barrel is held by the first holding portion. The second holding portion has the configuration of holding members other than the distal portion of the lens barrel which constitutes the observation unit. Here, the first holding portion and the second holding portion are at positions separated as far as possible in the axial direction of the mounting hole, and the holding lengths of the observation unit in the first and second holding portions are preferably set to be almost the same in order to reduce any interference with the connection pipe. Here, almost the same length means that the ratio of the holding length of the second holding portion to the holding length of the first holding portion is 0.3 to 2.7.

In order to hold the distal portion of the lens barrel, the first holding portion has the same circular shape generally as the profile of the lens barrel on which objective lenses are mounted. However, the second holding portion does not need to be circular, and can be formed into a shape conforming to the profile of a member held by the second holding portion. For example, if the member to be held by the second holding portion is a circular member, the second holding portion can be circular, and if the member to be held is an angular member, the second holding portion can be angular. In a case where the observation unit is configured such that the prism holder and the prism are joined to the lens barrel and the prism is provided with a solid state imaging element and its printed circuit board, the prism holder or the prism can be held so as to be inserted into the second holding portion. Here, the diameter of the first holding portion is smaller than the diameter of the second holding portion, and a space can be formed between the first and second holding portions as the mounting hole and the lens barrel are separated from each other between the first and second holding portions. Although this space can also conform to the shape of the second holding portion, this space may have a shape different from the second holding portion. In the lens barrel, a space which can be moved in the direction intersecting the axis of the lens barrel, i.e., in the direction separated from the connection pipe can be secured within this space. Also, when the lens barrel is detached from the first holding portion in taking out the observation unit from the distal portion, this lens barrel can be taken out from the distal portion so as to be lifted in the direction separated from the connection pipe. Additionally, even in a direct-viewing-type endoscope, similarly, the observation unit can be pulled out to the proximal side, avoiding the connection pipe.

Specifically, in the observation unit, the diameter of the first holding portion is smaller than the diameter of the second holding portion in the distal portion of the lens barrel and the proximal portion of the lens barrel in the axial direction. Therefore, a difference is caused in the external diameter or shape of the lens barrel which engages the first and second holding portions. Here, as a means for giving a difference to the external diameter or shape, it is possible to adopt either a configuration in which the difference is provided by a single member or a configuration in which the difference is provided by at least two members. For example, when the lens barrel has a tubular shape, a cylindrical region having a larger diameter than the distal portion of the lens barrel can be provided on the proximal side. Additionally, the lens barrel may not be circular but can also be a profile portion larger than the external diameter of the lens barrel. The distal portion of the lens barrel is held by the first holding portion, and a region having a larger profile than the distal portion is held in the second holding portion. Accordingly, the lens barrel can be configured by a first lens barrel portion on the smaller-diameter side and a second lens barrel portion on the larger-diameter side. Although objective lenses are mounted on the first lens barrel portion, in terms of providing the second lens barrel portion, some of the objective lenses may be provided, and some of the objective lenses may not be provided. Also, a special member can be provided within the region equivalent to the second lens barrel portion, and an optical component can also be provided within the region.

When the observation unit is mounted on the mounting hole, the observation unit is stably held, and when the observation unit is removed, the unit does not interfere with the connection pipe.

DESCRIPTION OF THE PREFERRED EMBODIMENTS

Figure 1:
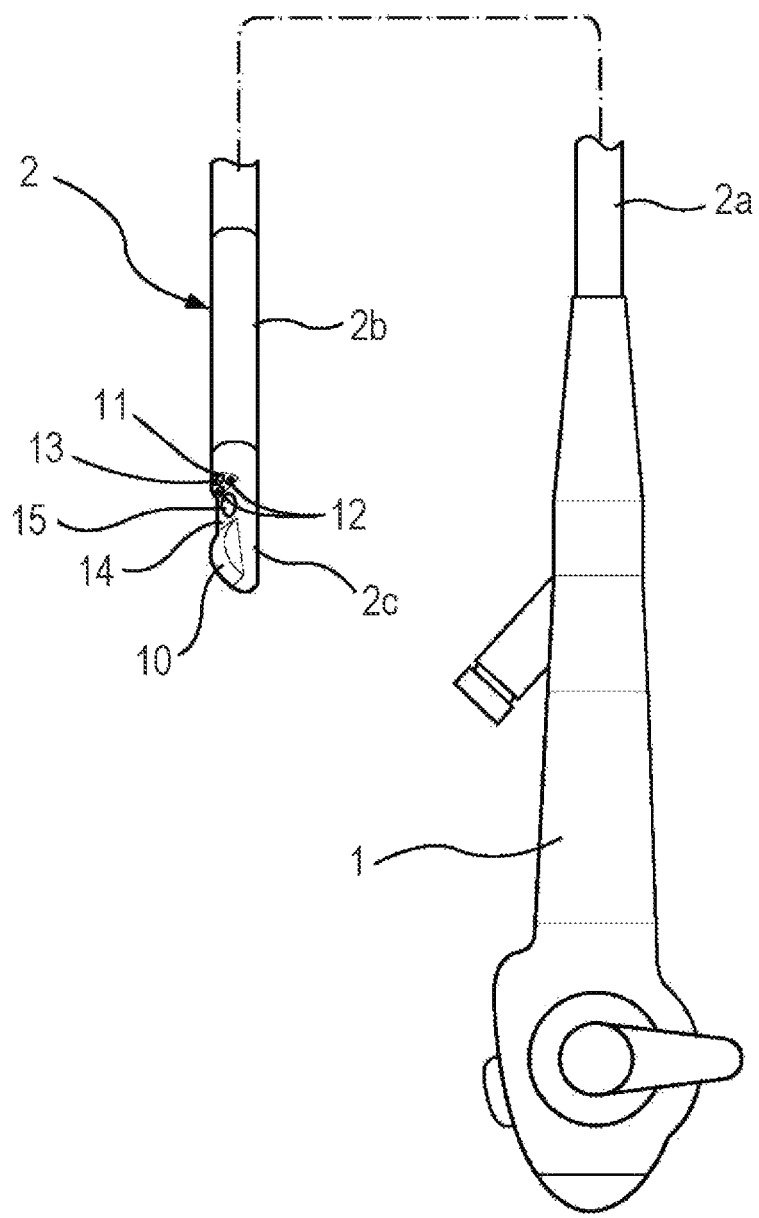
FIG. 1 is an appearance view showing an example of an ultrasonic endoscope of the present invention.

Hereinafter, embodiments of the present invention will be described with reference to the drawings. First, the overall configuration of an ultrasonic endoscope is shown in FIG. 1. In this drawing, reference numeral 1 designates a main body operating part, and reference numeral 2 designates an insertion part into a body cavity. The insertion part 2 includes a flexible portion 2a, a bending portion 2b, and a distal portion 2c which are continuously provided in this order at the main body operating part 1. In the insertion part 2, the longest portion is the flexible portion 2a, and the bending portion 2b is adapted so as to be capable of being bent and operated up and down or up and down and right and left. In addition, "up" indicates being directed to the ultrasonic observation mechanism side, and "down" indicates the opposite direction of "up". Additionally, "left" indicates the left side toward the distal portion 2c, and "right" indicates the right side toward the distal portion 2c.

Figure 2:
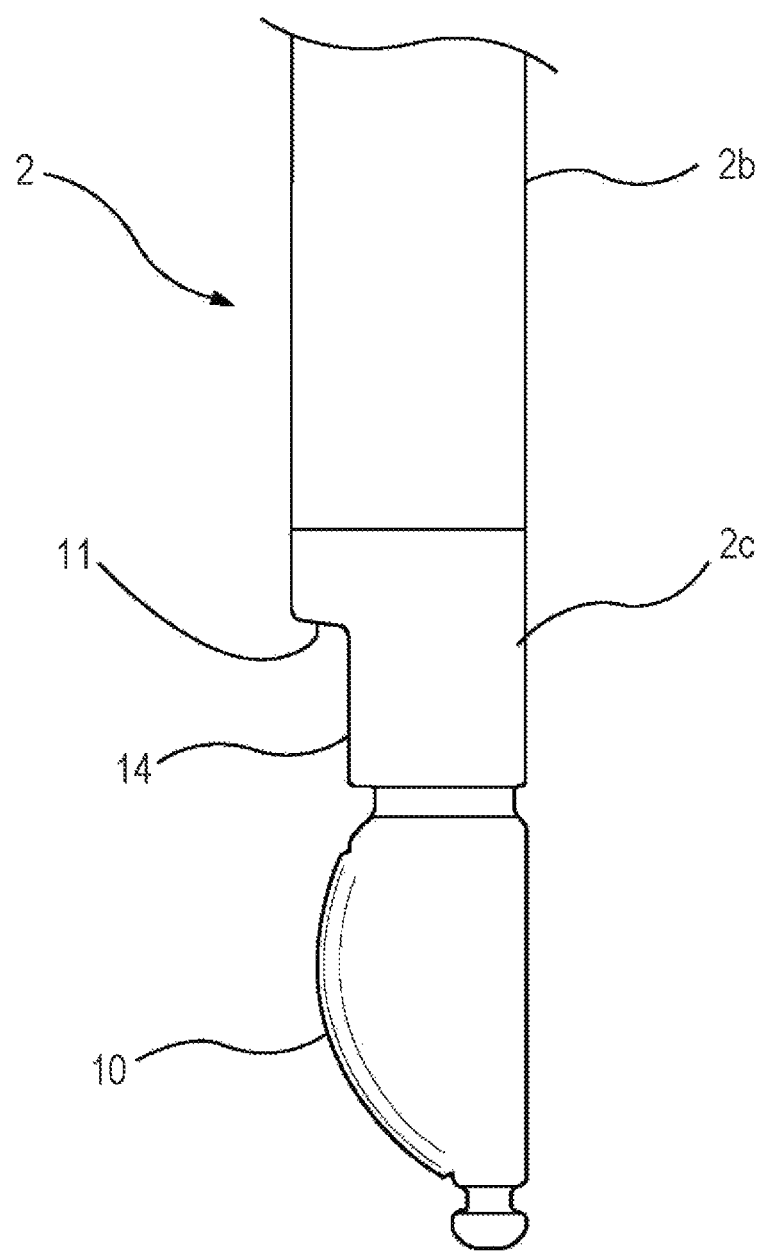
FIG. 2 is a left side view of the distal portion of an insertion part.
Figure 3:
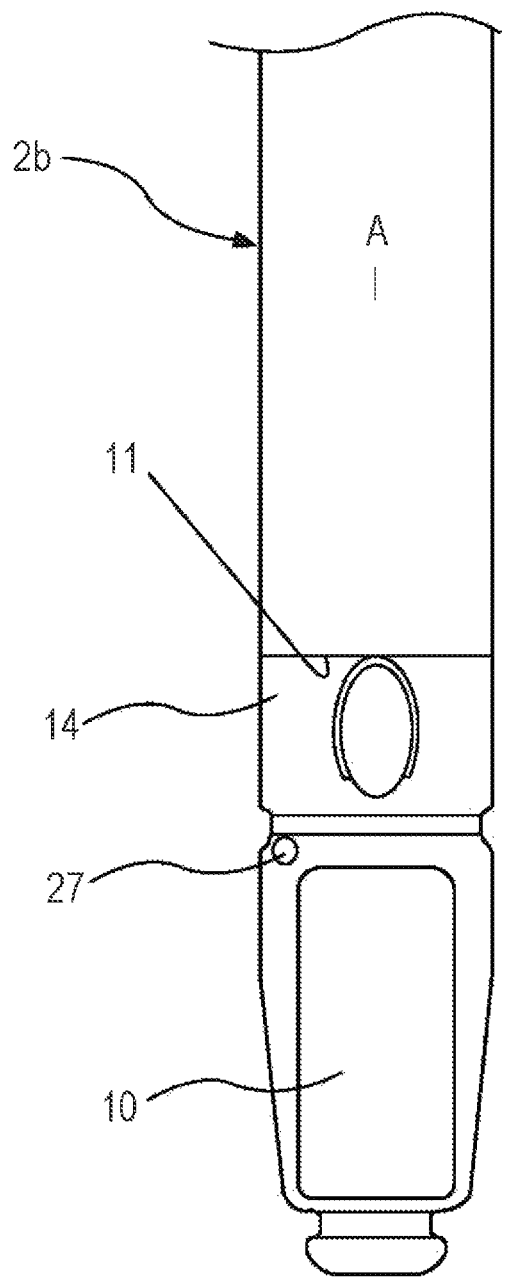
FIG. 3 is a plan view of FIG. 2.
Figure 4:
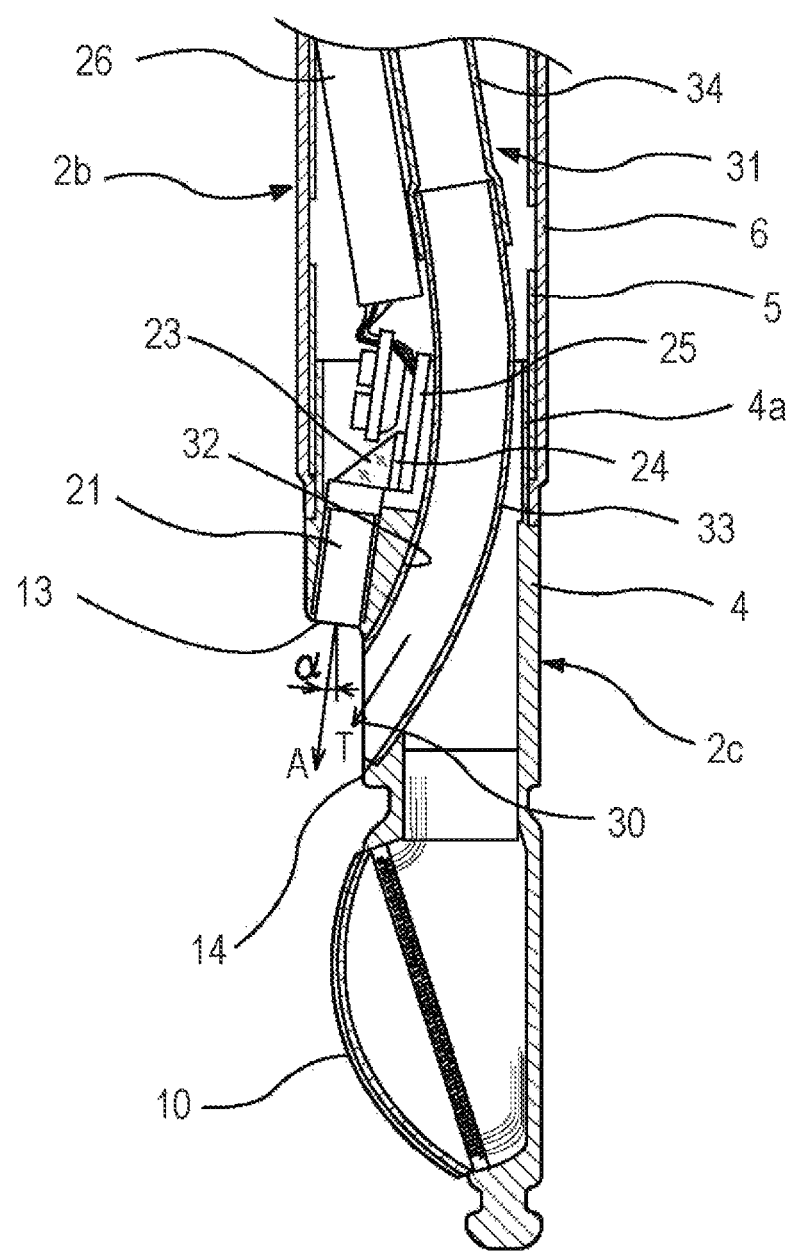
FIG. 4 is a cross-sectional view taken along the line A-A of FIG. 3.

As shown in FIGS. 2 to 4, the distal end body 4 is composed of the distal portion 2c, the ultrasonic observation mechanism provided at the foremost portion thereof, an endoscope observation mechanism, and a treatment tool insertion passage 32. The ultrasonic observation mechanism has an ultrasonic transducer 10, and the ultrasonic transducer 10 is configured by arranging a number of ultrasonic vibrators in the axial direction of the distal portion 2c. The arrangement has a convexly curved shape, and thereby, electronic convex scanning is performed. Additionally the distal portion 2c is made of a harder member than the flexible portion 2a and the bending portion 2b.

Additionally, a rising surface 11 is located closer to the proximal side than the disposed position of the ultrasonic transducer 10 in the distal end body 4. As shown in FIG. 1, the rising surface 11 is provided with a pair of illumination portions 12 and an observation portion 13 provided in the vicinity of the illumination portions 12, and the endoscope observation mechanism is constituted by these portions. The emitting end of a light guide (not shown) faces the illumination portions 12. Additionally, as shown in FIG. 4, an observation unit 20 is mounted on the observation portion 13. The observation unit 20 is constituted by a lens barrel 21 on which objective lenses are mounted, a prism holder 22 and a prism 23 which are joined to the end of the lens barrel 21, and a solid state imaging element 24 and its printed circuit board 25 which constitutes an imaging section, and a distribution cable 26 is connected to the printed circuit board 25. The prism 23 is provided to bend the optical axis of the objective lenses provided in the lens barrel 21 by 90 degrees, and thereby, the observation unit 20 becomes compact.

In the distal end body 4, a planar portion 14 is provided between the ultrasonic transducer 10, and the rising surface 11 provided with the endoscope observation unit, and a treatment tool outlet 30 opens to the planar portion 14. The treatment tool outlet 30 is an exit portion of a treatment tool insertion channel 31, and a puncture treatment tool, which is inserted into the inside of the body to perform treatment, such as sampling of cells or injection of a medical fluid, is also lead out of the treatment tool outlet 30. The treatment tool insertion channel 31 is constituted by the treatment tool insertion passage 32 formed in the distal end body 4, a connection pipe 33 whose distal side is inserted and fitted to the treatment tool insertion passage 32, and a treatment tool insertion tube 34 which is fitted to the proximal end of the connection pipe 33. Here, the treatment tool insertion tube 34 is constituted by a resin tube having flexibility in the bending direction, and the connection pipe 33 is made of a hard material, for example, metal or the like.

The lead-out direction of the treatment tool from the treatment tool insertion channel 31 is the direction of the arrow T shown in FIG. 4. Accordingly, when the puncture treatment tool is led out of the treatment tool outlet 30, the treatment tool enters the range of the visual field observed by the endoscope observation mechanism. Additionally, when the puncture treatment tool is inserted into a tissue in the body in a state in which the ultrasonic transducer 10 abuts on the inner wall of a body cavity directly or via a balloon, this puncture treatment tool enters the range of the ultrasonic observation visual field. Thereby, the puncture treatment tool is always placed under the monitoring of either the endoscope observation mechanism or the ultrasonic observation mechanism.

Here, in the following descriptions, with the axial direction of the distal portion 2c as a basis, the side where the ultrasonic transducer 10 is provided, i.e., the distal side is defined as the front side, and the connection side to the bending portion 2b, i.e., the proximal side is defined as the rear side. In the direction orthogonal to the axis, the side where the observation unit 20 is disposed and the treatment tool outlet 30 opens is defined as the upper side, and the opposite side thereof is defined as the lower side.

As shown in FIG. 4, the treatment tool insertion channel 31 is constituted by the treatment tool insertion tube 34, in the regions of the flexible portion 2a and the bending portion 2b in the insertion part 2, and the treatment tool insertion tube 34 extends in the axial direction of the insertion part 2. In the distal portion 2c, the treatment tool insertion channel 31 is constituted by the treatment tool insertion passage 32. The treatment tool insertion passage 32 opens to the planar portion 19 of the distal end body 4, and inclines obliquely forward and upward with respect to the axis of the insertion part 2. Accordingly, the connection pipe 33 is curved so as to protrude toward the lower side in order to smoothly perform formation of a passage to the treatment tool insertion passage 32 from the treatment tool insertion tube 34 made to extend in the axial direction. The treatment tool insertion passage 32 extends obliquely downward, and the connection pipe 33 extends up to the position of the treatment tool outlet 30 in the treatment tool insertion passage 32 or up to a position close to the treatment tool outlet. Also, a proximal end of the connection pipe 33 protrudes by a predetermined length rearward from the distal end body 4, and this protruding region is curved.

The observation unit 20 which constitutes the endoscope observation mechanism is fixed to and held by the distal end body 4. As shown in FIG. 4, the observation visual field is the oblique front field, and the axis A of the lens barrel 21 of the observation unit 20 which constitutes the endoscope observation mechanism is inclined by an angle α shown in FIG. 4 with respect to the direction parallel to the axis of the insertion part 2.

Figure 5:
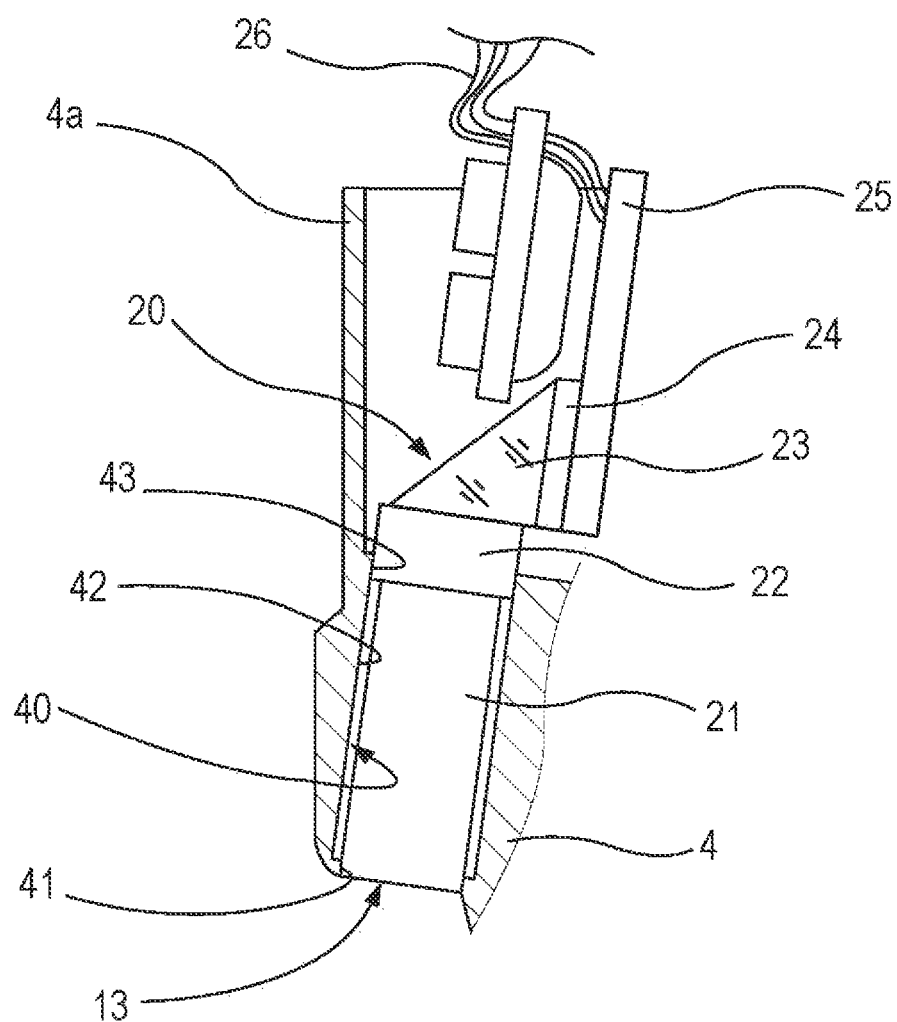
FIG. 5 is an enlarged view of essential parts of FIG. 4.

The configuration of a mechanism which fixes the observation unit 20 to the distal end body 4 is shown in FIG. 5. In order to mount the observation unit 20, a mounting hole 40 is bored in the distal end body 4. The mounting hole 40 is provided so as to be inclined by an angle α with respect to the axis A of the insertion part 2 from the position where the mounting hole opens to the rising surface 11 of the distal end body 4, and a first holding portion 41 is provided on the front side of the mounting hole 40. The first holding portion 41 holds the lens barrel 21, and the holding length thereof is shorter than the length of the lens barrel. A second holding portion, which is formed so as to have a greater diameter than the diameter of the first holding portion 41, is provided on the rear side of the first holding portion 41. A space 42 is formed between the first and second holding portions as the mounting hole and the lens barrel are separated from each other. The region on the distal side of the prism holder 22 which connects together the lens barrel 21 and the prism 23 is fitted into the second holding portion 43. The region between the first holding portion 41 and the lens barrel 21 and the region between the second holding portion 43 and the prism holder 22 are adhered and fixed with an adhesive or the like.

Here, although the length by which the first and second holding portions 41 and 43 hold the observation unit 20 is set from a viewpoint of the stability of holding, the ratio of the holding length of the second holding portion 43 to the holding length of the first holding portion 41 is preferably 0.3 to 2.7. Additionally, the difference between the lengths may be about ±0.5 mm, and is preferably about ±0.2 mm, and the lengths are more preferably made the same. Additionally, as for the space 42, the space where the observation unit 20 can be tilted up and down is secured in a state where the distal portion of the lens barrel 21 is located within this space. The cross-sectional shape of the space 42 may be a shape similar to either the lens barrel 21 or the prism holder 22 inserted into the second holding portion 43, or may be a shape which is not similar thereto.

The rear side of the distal end body 4 becomes a tubular portion 4a, and a distal ring 5 is fitted into the tubular portion 4a. Moreover, the front end of a shell layer 6 of the bending portion 2b extends up to the region on the proximal side of the distal end body 4, and is fixed by spooling and adhesion. Accordingly, when the adhered portion is peeled off and the wound thread is cut, the shell layer 6 can be pulled in toward the bending portion 2b, and the fitting between the tubular portion 4a of the distal end body 4 and the distal ring 5 can be released in this state.

In the ultrasonic endoscope configured as described above, repairing or checking of the observation unit 20, the ultrasonic transducer 10, and the like, which are provided at the distal portion 2c in the insertion part 2, can be performed as necessary.

In order to remove the observation unit 20 from the mounting hole 40 of the distal end body 4, the adhesive of the abutting surface between the observation unit 20 and the mounting hole 40 is peeled off. Then, the observation unit 20 is moved along the mounting hole 40. Since the prism holder 22, the prism 23 and the solid state imaging element 24 and its printed circuit board are provided on the rear side of the observation unit 20, the observation unit 20 fixed to the mounting hole 40 cannot be pulled out to the distal side. For this reason, the observation unit 20 is pushed in toward the rear side.

As shown in FIG. 4, the distal portion of the lens barrel 21 is held by the first holding portion 41 of the mounting hole 40, and the distal portion of the prism holder 22 is held by the second holding portion 43. The lengths by which the first and second holding portions 41 and 43 are held are shorter than the length of the lens barrel, and the observation unit 20 can be almost simultaneously detached from the first and second holding portions 41 and 43 simply by moving the observation unit 20 slightly. As a result, since the region of the observation unit 20 closer to the rear side than the prism holder 22 moves to the internal space of the tubular portion 4a of the distal end body 4, the diameter of the first holding portion is smaller than the diameter of the second holding portion and the mounting hole and the lens barrel are separated from each other, the lens barrel 21 is located within the space 42 larger than the external diameter thereof. For this reason, the observation unit 20 can be inclined such that the rear side of the observation unit 20 faces the upper side with the vicinity of a portion on the lens barrel corresponding to the second holding portion 43 as a center. Alternatively, the overall observation unit can be lifted to the upper side as it is, and can be moved in a direction almost parallel to the connection pipe 33 or in a direction separated from the connection pipe 33. By moving the observation unit 20 rearward, the observation unit 20 can be separated from the mounting hole 40 of the distal end body 4 without interfering with the connection pipe 33. Here, since the diameter of the first holding portion is smaller than the diameter of the second holding portion, the opening of the second holding portion 43 is wider than the first holding portion 41. As a result, the second holding portion 43 does not hinder lifting the observation unit 20 upward.

Additionally, in order to assemble the observation unit 20 again, the lens barrel 21 is inserted into the first holding portion 41 through the space 42 from the second holding portion 43 in a state where the observation unit 20 is separated from the connection pipe 33. In this case, immediately before being inserted into the first holding portion 41, a rear region of the observation unit 20, i.e., the regions of the solid state imaging element 24 and its printed circuit board 25 can be held in the state of being separated from the connection pipe 33. Moreover, when the lens barrel 21 is inserted into the first holding portion 41, the front side of the observation unit 20 is directed obliquely downward. Then, almost simultaneously when the distal portion of the lens barrel 21 is inserted into and held by the first holding portion 41, the prism holder 22 is inserted into and held by the second holding portion 43. Then, two holding portions of the holding portions 41 and 43 are fixed to the lens barrel using an adhesive.

As described above, in a case where the holding lengths of the lens barrel 21 by the first holding portion 41 and the second holding portion 43 are the same, the proximal end of the observation unit 20 and the connection pipe 33 may be separated from each other by the holding length of the lens barrel 21 by the first holding portion 41. In a case where the holding lengths of the lens barrel 21 by the first holding portion 41 and the second holding portion 43 are different from each other, the proximal end of the observation unit 20 and the connection pipes 33 may be separated from each other at least by the larger of the lengths. Thereby, the length of a hard portion of the distal portion 2c including the overall length of the distal end body 4 and the distal ring 5 fitted into the tubular portion 4a of the distal ends body can be shortened, and the operability of the operation of inserting the insertion part 2 into a body cavity can be improved. Additionally, since the observation unit 20 is fixed to the distal end body 4 in two places of the distal side and rear end thereof, the observation unit 20 can be stably held.

Figure 6:
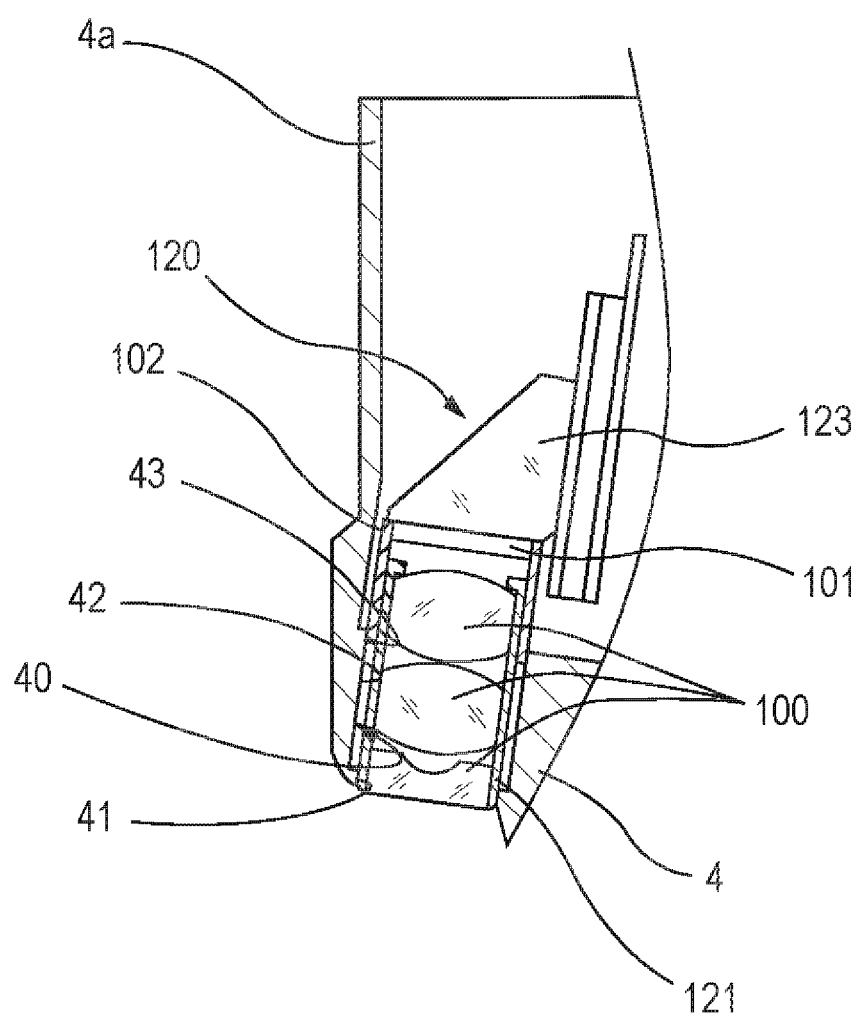
FIG. 6 is a cross-sectional view showing a second embodiment of the present invention.

In the aforementioned embodiment, although the configuration in which the distal portion of the lens barrel 21 is held by the first holding portion 41, and the distal portion of the prism holder 22 is held by the second holding portion 43 is adopted, an observation unit 120 shown in FIG. 6 can also be used. The observation unit 120 has a lens barrel 121 on which objective lenses 100 are mounted, and a holder tube 102 into which the lens barrel 121 is inserted and a correction filter 101 is fitted. The correction filter 101 is joined to a prism 123. In this case, a distal portion of the lens barrel 121 is held by the first holding portion 41, and a distal portion of the holder tube 102 is held by the second holding portion 43. Here, although the correction filter 101 mounts the holder tube 102, the holder tube may be provided with some of the objective lenses besides this correction filter. The lens barrel 121 on which the objective lenses 100 are mounted functions as a first lens barrel, and the holder tube 102 functions as a second lens barrel.

Figure 7:
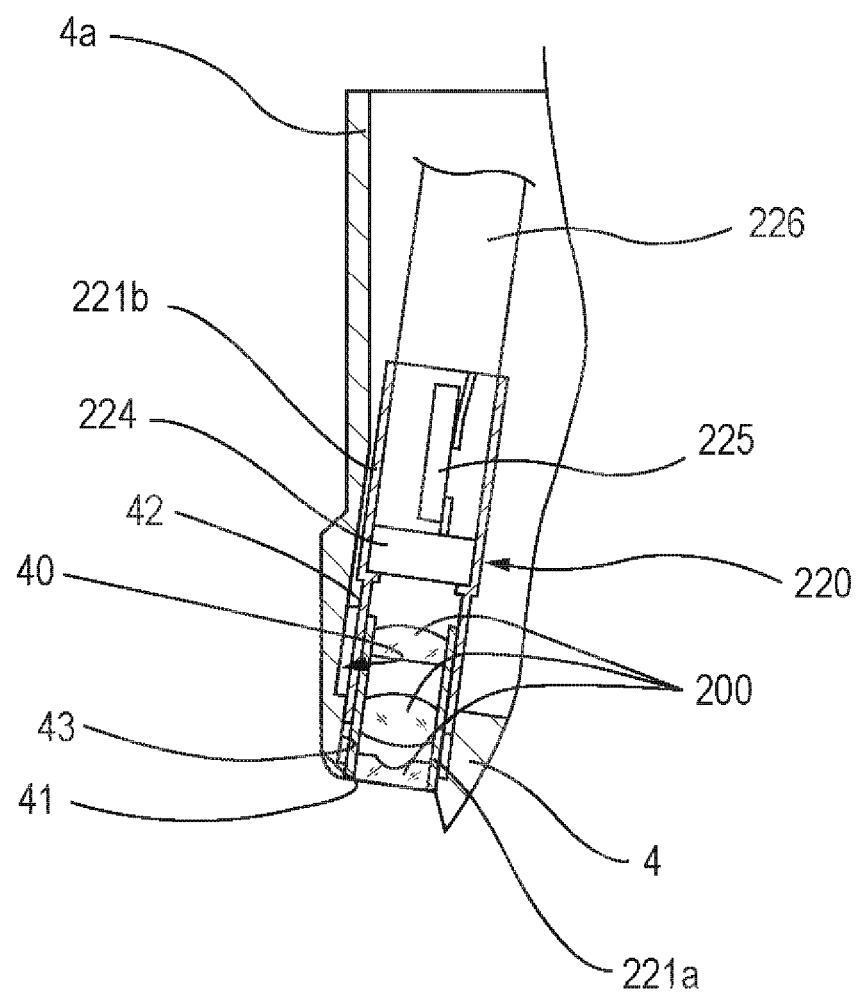
FIG. 7 is a cross-sectional view showing a third embodiment of the present invention.

Additionally, although both the aforementioned respective observation units 20 and 120 provide the prisms 23 and 123, an observation unit 220 shown in FIG. 7 has a configuration in which a solid state imaging element 224 is provided in a direction orthogonal to the optical axis of objective lenses 200. The observation unit 220 is constituted by a first lens barrel 221a on which the objective lenses 200 is mounted, and a second lens barrel 221b on which the solid state imaging element 224 is mounted. In this case, a distal portion of the first lens barrel 221a is held by the first holding portion 41, and a distal portion of the second lens barrel 221b is inserted into the second holding portion 43. Here, a circuit printed circuit board 225 and a distribution cable 226 along with the solid state imaging element 224 are provided within the second lens barrel 221b.

Figure 8:
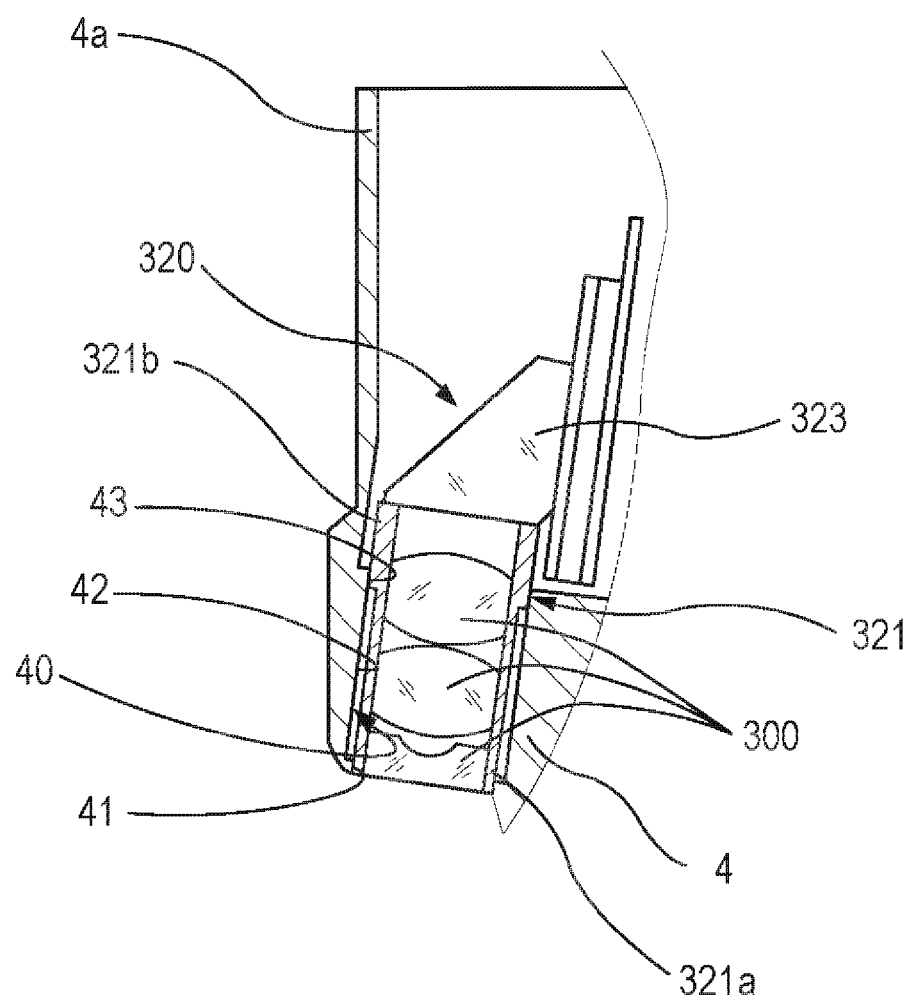
FIG. 8 is a cross-sectional view showing a fourth embodiment of the present invention.

Additionally, in an observation unit 320 shown in FIG. 8, a lens barrel 321 is stepped in order to apply the lens barrel to a configuration in which the diameter of the first holding portion is smaller than the diameter of the second holding portion. A smaller-diameter portion in which the diameter of the lens barrel is smaller is a first lens barrel portion 321a, and a larger-diameter portion in which the diameter of the lens barrel is larger than that of the smaller-diameter portion is a second lens barrel portion 321b. The second lens barrel 321b is joined to a prism 323, and a region on the front side on which the objective lenses 300 is mounted becomes the smaller-diameter portion 321a. Accordingly, a distal portion of the first lens barrel portion 321a of the lens barrel 321 is held by the first holding portion 41, and the second lens barrel portion 321b is held by the second holding portion 43.

Figure 9:
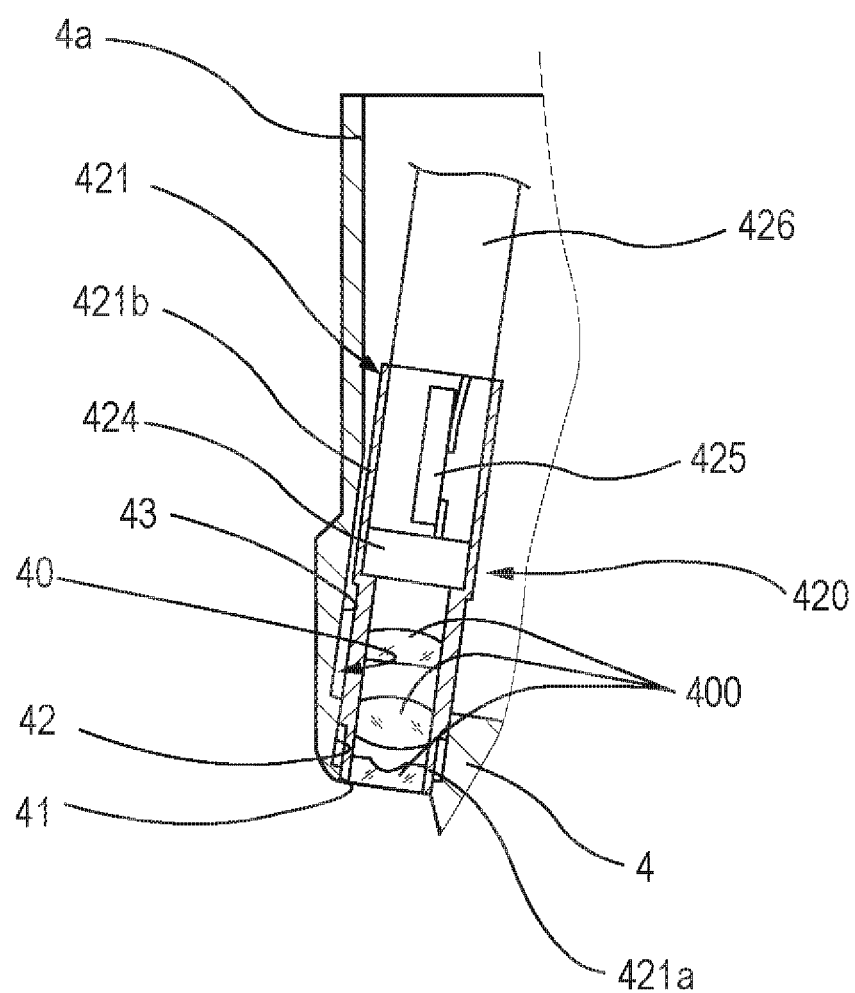
FIG. 9 is a cross-sectional view showing a fifth embodiment of the present invention.

Moreover, FIG. 9 shows that a first lens barrel portion 421a on which objective lenses 400 are mounted is inserted into the first holding portion 41 in the mounting hole 40, and a second lens barrel portion 421b in which a printed circuit board 425 and a distribution cable 426 along with the solid state imaging element 424 are provided are formed as a lens barrel 421, in the configuration shown in FIG. 7.

In addition, needless to say the above correspondence between the drawings and the present inventions in the claims is illustrated for reference, and the present invention can be variously changed unless such change digress from the spirit of the present invention.

What is claimed is:

1. An endoscope comprising:
   an insertion part having a distal portion, a bending portion connected to the distal portion and a flexible portion connected to the bending portion and having more flexibility than the distal portion,
   a main body operating part,
   an observation unit including a lens barrel on which objective lenses are mounted, and imaging section disposed at the imaging position of the objective lenses,
   a mounting hole disposed at the distal portion for mounting the observation unit on the distal portion by inserting the lens barrel,
   a first supporting structure that is provided on an inner wall of the mounting hole and supports a distal side of the lens barrel from outside of the lens barrel,
   a second supporting structure that is provided on an inner wall of the mounting hole and supports a proximal side of the lens barrel from outside of the lens barrel,
   a cavity disposed between the first supporting structure and the second supporting structure which separates an inner wall of the mounting hole from a periphery of the lens barrel, and
   an ultrasonic observation mechanism provided on the distal portion, which irradiates ultrasonic waves to an observation area which is set diagonally forward, and acquires a ultrasonic image of the observation area based on reflected waves of irradiated ultrasonic waves,
   wherein the lens barrel is supported by the first supporting structure and the second supporting structure in a state where an optical axis of the objective lenses is inclined with respect to a longitudinal direction of the insertion part so that an imaging area of the imaging section overlaps the observation area of the ultrasonic observation mechanism,
   a distribution cable is inserted inside the insertion part from the observation unit to a back side of the insertion part along the longitudinal direction,
   in case of detaching the observation unit from the distal portion, the observation unit is pulled to the back side of the insertion part where a space for inserting the distribution cable is formed, and
   in a case where the observation unit is released from the first supporting structure by pulling the observation unit to the space, the lens barrel rotates so that the optical axis of the objective lenses is coincident with the longitudinal direction of the insertion part by moving the distal side of the lens barrel to the cavity.

2. The endoscope according to claim 1,
   wherein the distal portion further comprises a treatment tool insertion channel through which a treatment tool is led out of a treatment tool outlet and a treatment tool insertion channel leads a treatment tool out of the treatment tool outlet obliquely forward.

3. The endoscope according to claim 2,
   wherein an axial length of the mounting hole where the first supporting structure and the observation unit come into contact with each other is equal to an axial length of the mounting hole where the second supporting structure and the observation unit come into contact with each other.

4. The endoscope according to claim 2,
   wherein the lens barrel comprises a first lens barrel held by the first supporting structure, and a second lens barrel is circumscribed on the first lens barrel and having a larger external diameter than the first lens barrel.

5. The endoscope according to claim 4,
   wherein the observation unit further comprises a prism, and the second lens barrel is a prism holder which connects the first lens barrel and the prism together.

6. The endoscope according to claim 4,
   wherein the second lens barrel is a holder which connects the first lens barrel and the imaging section together.

7. The endoscope according to claim 2,
   wherein a first diameter of a portion of the lens barrel held by the first supporting structure is smaller than a second diameter of a portion of the lens barrel held by the second supporting structure.

8. The endoscope according to claim 2,
   wherein the lens barrel is reduced in diameter toward the distal portion from a side separated from the distal portion.

9. The endoscope according to claim 2,
   wherein a prism is provided within a portion of the lens barrel held by the second supporting structure.

10. The endoscope according to claim 1,
    wherein an axial length of the mounting hole where the first supporting structure and the observation unit come into contact with each other is 0.3 to 2.7 times an axial length of the mounting hole where the second supporting structure and the observation unit come into contact with each other.

11. The endoscope according to claim 2,
    wherein an axial length of the mounting hole where the first supporting structure and the observation unit come into contact with each other is 0.3 to 2.7 times an axial length of the mounting hole where the second supporting structure and the observation unit come into contact with each other.

12. The endoscope according to claim 1,
    wherein an axial length of the mounting hole where the first supporting structure and the observation unit come into contact with each other is equal to an axial length of the mounting hole where the second supporting structure and the observation unit come into contact with each other.

13. The endoscope according to claim 1,
wherein the lens barrel comprises a first lens barrel held by the first supporting structure, and a second lens barrel is circumscribed on the first lens barrel and having a larger external diameter than the first lens barrel.

14. The endoscope according to claim 13,
wherein the observation unit further comprises a prism, and the second lens barrel is a prism holder which connects the first lens barrel and the prism together.

15. The endoscope according to claim 13,
wherein the second lens barrel is a holder which connects the first lens barrel and the imaging section together.

16. The endoscope according to claim 13,
wherein a diameter of the second supporting structure is same as the diameter of the second lens barrel, and
the second supporting structure directly supports the second lens barrel.

17. The endoscope according to claim 1,
wherein a first diameter of a portion of the lens barrel held by the first supporting structure is smaller than a second diameter of a portion of the lens barrel held by the second supporting structure.

18. The endoscope according to claim 1,
wherein the lens barrel is reduced in diameter toward the distal portion from a side separated from the distal portion.

19. The endoscope according to claim 1,
wherein a prism is provided within a portion of the lens barrel held by the second supporting structure.

20. The endoscope according to claim 1,
wherein a portion of the observation unit is fitted into the second supporting structure and held by the second supporting structure.

21. The endoscope according to claim 1, wherein
the first supporting structure is a supporting structure adjacent to a portion of the lens barrel on a side of the distal portion, and
the second supporting structure is another supporting structure, which is adjacent to a portion of the observation unit.

22. The endoscope according to claim 1, wherein the second supporting structure is located so as to be attached to a portion of the lens barrel that it supports.

23. An endoscope comprising:
an insertion part having a distal portion, a bending portion connected to the distal portion and a flexible portion connected to the bending portion and having more flexibility than the distal portion,
a main body operating part,
an observation unit including a lens barrel on which objective lenses are mounted, and imaging section disposed at the imaging position of the objective lenses,
a mounting hole disposed at the distal portion for mounting the observation unit on the distal portion by inserting the lens barrel,
a first supporting structure that is provided on an inner wall of the mounting hole and supports a distal side of the lens barrel from outside of the lens barrel,
a second supporting structure that is provided on an inner wall of the mounting hole and supports a proximal side of the lens barrel from outside of the lens barrel,
a cavity disposed between the first supporting structure and the second supporting structure which separates an inner wall of the mounting hole from a periphery of the lens barrel, and
a treatment tool insertion channel through which a treatment tool is led out of a treatment tool outlet formed at the distal portion from the main body operating part side via an inside of the insertion part,
wherein the treatment tool insertion channel is provided so as to cross a moving path of the observation unit when the observation unit is moved to a back side of a optical axis of the objective lenses,
a distribution cable is inserted inside the insertion part from the observation unit to a back side of the insertion part via a path different from the treatment tool insertion channel,
in case of detaching the observation unit from the distal portion, the observation unit is pulled to a space where the distribution cable is inserted so as to avoid interference with the treatment tool insertion channel, and
in a case where the observation unit is released from the first supporting structure by pulling the observation unit to the space, the lens barrel rotates so that the optical axis of the objective lenses is coincident with the longitudinal direction of the space by moving the distal side of the lens barrel to the cavity.

* * * * *